(12) United States Patent
Sheen et al.

(10) Patent No.: US 6,279,378 B1
(45) Date of Patent: Aug. 28, 2001

(54) ULTRASONIC GAS ANALYZER AND METHOD TO ANALYZE TRACE GASES

(75) Inventors: Shuh-Haw Sheen; Hual-Te Chien, both of Naperville; Apostolos C. Raptis, Downers Grove, all of IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/428,505

(22) Filed: Oct. 27, 1999

(51) Int. Cl.[7] .................................................. G01N 29/02
(52) U.S. Cl. ..................... 73/24.01; 73/24.06; 73/24.05; 73/597
(58) Field of Search ............................... 73/61.29, 61.49, 73/61.79, 61.75, 24.05, 64.53, 24.06, 24.01, 600, 597; 123/350, 740, DIG. 13, 395, 402

(56) References Cited

U.S. PATENT DOCUMENTS

| | | | |
|---|---|---|---|
| 4,574,615 | * 3/1986 | Bower et al. | 73/24.01 |
| 5,060,514 | * 10/1991 | Aylsworth | 73/24.01 |
| 5,351,522 | * 10/1994 | Lura | 73/597 |
| 5,497,661 | * 3/1996 | Stripf et al. | 73/611 |
| 5,537,854 | * 7/1996 | Phillips et al. | 73/24.01 |
| 5,581,014 | * 12/1996 | Douglas | 73/24.01 |
| 5,625,140 | * 4/1997 | Cadet et al. | 73/24.01 |
| 5,644,070 | * 7/1997 | Gibboney et al. | 73/24.01 |

* cited by examiner

Primary Examiner—Hezron Williams
Assistant Examiner—Michael Cygan
(74) Attorney, Agent, or Firm—Mason, Kolehmainen, Rathburn & Wyss

(57) ABSTRACT

An ultrasonic gas analyzer includes an acoustic cavity through which an air sample is drawn by a low speed air pump or other mechanism. The cavity has a pair of ultrasonic wave transmitters/receivers on opposite sides of the acoustic cavity. An electronic circuit controls the transmitters/receivers so that a high frequency ultrasonic wave is propagated across the cavity and thereby through the gas flowing through the cavity. This ultrasonic wave reflects back and forward across the acoustic cavity and the transmitters/receivers receive this wave and supply a signal indicative of the wave to an electronic circuit. Based on the time of flight data for the ultrasonic wave being reflected in a gas/air mixture and in air and the amplitude of those reflected ultrasonic waves, a determination is made as to the gases within the gas/air mixture. This determination then can be displayed and an audio signal can be generated depending on the amount of detected gases. In one embodiment of the gas analyzer, a switch valve is used to selectively provide the gas/air mixture or air through the acoustic cavity. In another embodiment of the gas analyzer, two acoustic cavities are provided with a double concave reflector lens separating the cavities and each with a transducer at an opposite end from the lens. Air is drawn through one of the acoustic cavities and the gas/air mixture is drawn through the other of the acoustic cavities

24 Claims, 4 Drawing Sheets

ULTRASONIC GAS ANALYZER AND METHOD TO ANALYZE TRACE GASES

CONTRACTUAL ORIGIN OF THE INVENTION

The United States Government has rights in this invention pursuant to Contract No. W-31-109-ENG-38 between the United States and The University of Chicago.

BACKGROUND OF THE INVENTION

1. Field of the Invention

The present invention relates to an ultrasonic apparatus and a method utilizing ultrasonic waves for analyzing gases so as to measure trace amounts of gases in an air sample, and more particularly, to a new and improved ultrasonic apparatus and a method utilizing ultrasonic waves to measure amounts of gases in a gas/air mixture by comparing the sound velocity and acoustic attenuation of sound waves traveling through the gas/air mixture to the sound velocity and acoustic attenuation of sound waves traveling through air.

2. Background of the Invention

The measurement of trace amounts of gases mixed in air is needed in a number of different applications. For example, a portable field instrument can be used to detect and locate helium leaks from a component in which helium gas is used. In this regard, the instrument could be used for field inspection of potential leaks from a jet fuel-cell. While methods using ultrasonic waves have been used for characterizing gases, no ultrasonic instruments have been built specifically for detecting trace gases in a gas mixture. Moreover, inexpensive and portable gas analyzers are not readily available.

Another example where instruments are needed to measure trace amounts of gases in air is in the exhaust from a diesel engine. In such exhausts, unburnt carbon and volatile matter, such as hydrocarbons and inorganic species, are agglomerated to form particles of submicron size. These submicron size particles need to be monitored because the submicron particles are likely to cause health concerns due in part to their long suspension time in air. Diesel and compression ignition direct injection (CIDI) engines offer higher thermal efficiency than spark-ignited gasoline engines, but such engines tend to suffer from high emissions of $NO_X$ and particles. As a result, a significant amount of research has been directed to controlling the $NO_X$ and particulate matter (PM) emissions from light-duty vehicles. Consequently, low-cost and reliable emission sensors are needed in connection with the development of ways to control these emissions.

Optical techniques have been used for particulate monitoring. Measurements of light attenuation and scattering are generally used to determine particle concentration and size distribution, respectively. These optical techniques tend to be impractical for use in connection with the exhaust from a CIDI engine because of the complexity of the sensor design, the high costs of such devices and the hostile environment in the exhaust line of a CIDI engine where the gases need to be detected. In fact, such optical techniques tend to be limited to laboratory applications because of practical problems with such optical devices such as vibration effects on the light source and surface contamination of optical windows.

Yet another situation where detection and measurement of hydrogen gas is necessary is in connection with fuel cells. Fuel cells use energy more efficiently and produce less emissions that may pollute the environment. Those cells utilize hydrogen gas produced from alternate energy fuel to generate usable electrical energy which can be used to power automobiles or domestic appliances. However, those fuel-cells need to be closely monitored with respect to the flow of hydrogen to ensure the safe and efficient operation of the fuel-cell power system. Hydrogen sensors that have been typically used are based on electrochemical principles. However, these types of sensors cannot be used with such fuel-cell systems because of slow response time, interference from other reducing gases (e.g., CO), and lack of sensitivity to high concentrations of those gases. In this latter regard, typical hydrogen concentration in a fuel-cell system is around 38%. Thermal conductivity and mass spectroscopy also can be utilized in measuring such hydrogen gas. However, these types of technologies have certain drawbacks. In the case of thermal conductivity, the measurements are flow rate dependent and in the case of mass spectroscopy, it requires an ionization source and a vacuum system.

Accordingly, it is an object of the present invention to provide a new and improved ultrasonic gas analyzer and a method to analyze trace gases using ultrasonic waves.

It is another object of the present invention to provide a new and improved ultrasonic apparatus and a method utilizing ultrasonic waves for analyzing gases so as to measure trace amounts of gases in an air sample by comparing the sound velocity and acoustic attenuation of the sound waves traveling through the gas/air mixture to the sound velocity and acoustic attenuation of the sound waves traveling through air alone.

It is still another object of the present invention to provide a new and improved ultrasonic apparatus and a method utilizing ultrasonic waves for analyzing gases so as to measure trace amounts of gases in an air sample by transmitting high frequency ultrasonic wave pulses through a gas sample flowing through an acoustic cavity and analyzing the speed of and attenuation of the pulsed waves traveling through the gas samples.

It is yet another object of the present invention to provide a new and improved ultrasonic apparatus for measuring trace amounts of gas in air that is low in cost, rugged and highly sensitive so as to be capable of detecting trace amounts of certain types of gases in an air sample.

SUMMARY OF THE INVENTION

In accordance with these and many other objects of the present invention, an ultrasonic gas analyzer includes an acoustic cavity through which an air sample is drawn by a low speed air pump or other mechanism. The cavity has a pair of ultrasonic wave transmitters/receivers or transducers, one on each opposite side of the acoustic cavity. An electronic circuit controls the transmitters/receivers so that a high frequency (e.g., 0.5 MHz) ultrasonic wave is propagated across the cavity and thereby through the gas flowing through the cavity. This ultrasonic wave reflects back and forward across the acoustic cavity and the transmitters/receivers on the opposite sides of the cavity receive this wave and supply a signal indicative of the wave to a pulser/receiver in the electronic circuit. The signal then is filtered to eliminate unwanted frequencies (such as noise) and the average of the signal over a number of cycles is determined. A gated peak detector and a timer counter enable the determination to be made as to the time of flight of the ultrasonic wave across the cavity. Based on a comparison of this time of flight data with the time of flight data of such ultrasonic waves when air is flowing through the cavity, a determination is made as to the trace amount of certain gases within the air. This determination then can be displayed and an audio signal can be generated if the amount of the detected gases is above a certain threshold level.

While the ultrasonic analyzer is relatively portable and cost effective, it nevertheless can provide information as to trace amounts of certain gases within the air flowing through the acoustic cavity. This is because the electronic circuitry does not analyze the first wave received by the transmitters/receivers but instead allows the wave to bounce back and forward across the cavity so that the effective travel length of the wave being analyzed is much longer than the width of the cavity.

In one embodiment of the present invention, the ultrasonic analyzer is used to determine trace amounts of helium in the gas mixture flowing through the acoustic cavity. In such an analyzer, a switch valve is used to selectively provide only air through the acoustic cavity so that a calibration reading can be taken of ambient air or so that air with helium gas mix therein is provided through the acoustic cavity.

In another embodiment of the present invention, the ultrasonic analyzer is used to determine amounts of hydrogen in the gas mixture flowing through the acoustic cavity. In such an analyzer, a switch valve is used to selectively provide only air through the acoustic cavity so that a calibration reading can be taken of ambient air or so that air with hydrogen gas mixed therein is provided through the acoustic cavity. In addition, a thermocouple can be used to provide thermal information as to the gases flowing through the acoustic cavity.

In yet another embodiment of the present invention, exhaust gases from an exhaust pipe of a CIDI engine flows through the acoustic cavity as a result of the connection of the acoustic cavity with the low pressure vacuum manifold of the engine. In this embodiment, a second acoustic cavity is provided with a double concave reflector lens separating the cavities. Each of the acoustic cavities has a transmitter/receiver on one side of the acoustic cavity and the opposite side of the cavity is formed by one of the sides of the reflector. A mixture of exhaust gases and air flows through the one acoustic cavity and ambient air flows through the other cavity. In this manner, the electronic circuit can continually compare the speed and amplitude of the sound waves through the exhaust gases/air mixture with the speed and amplitude of the sound waves through the air alone. Both the speed and amplitude changes are used to determine the amount of particulates in the exhaust gases.

BRIEF DESCRIPTION OF THE DRAWINGS

These and many other objects and advantages of the present invention will become readily apparent from consideration of the following detailed description of the embodiments of the invention shown in the accompanying drawing herein.

DETAILED DESCRIPTION OF THE PREFERRED EMBODIMENTS

Figure 1:
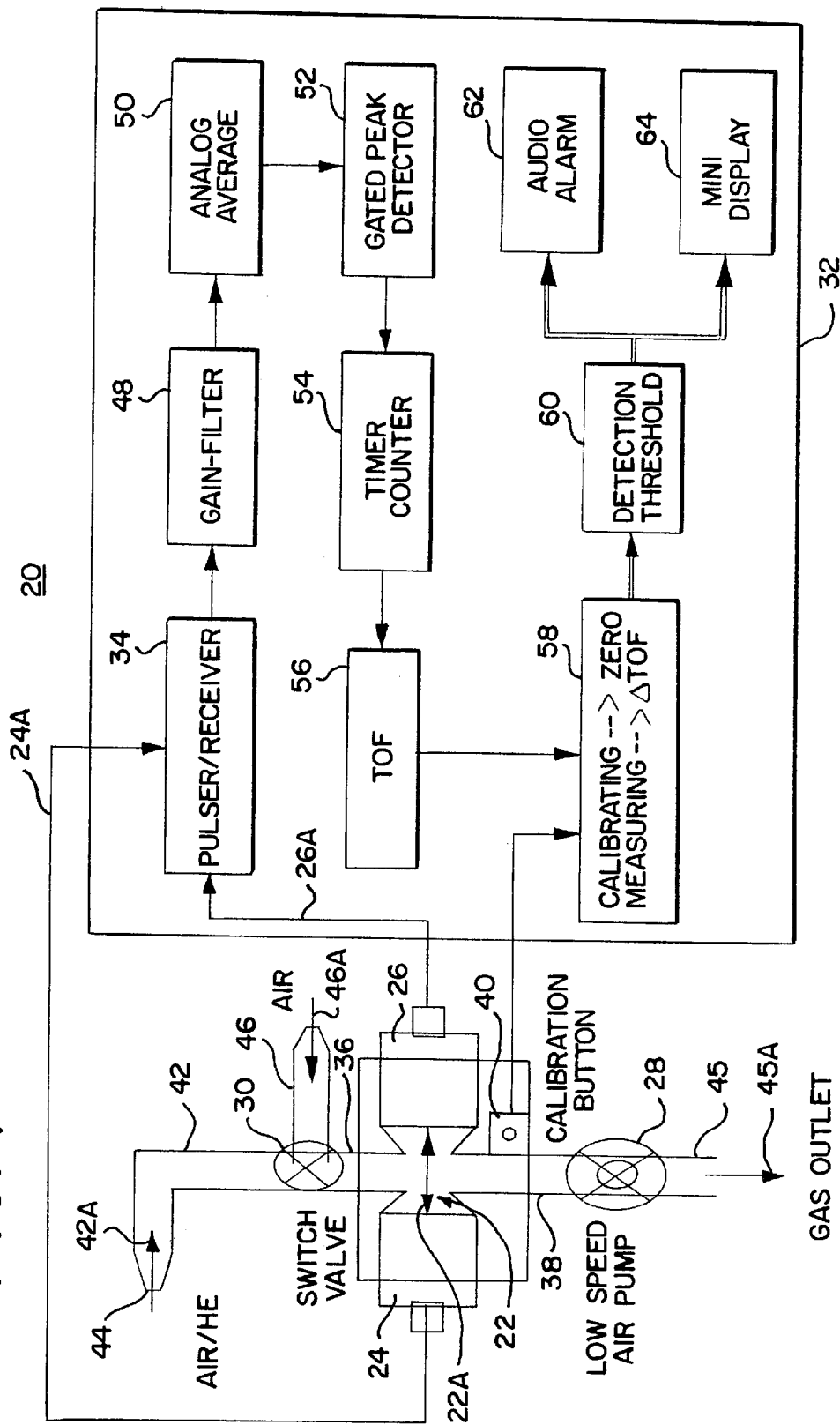
FIG. 1 is a diagrammatic view of an embodiment of the present invention which is an ultrasonic helium leak detector with the electronic circuit therefor shown in block diagram form.

Referring now more specifically to FIG. 1 of the drawings, therein is disclosed a diagrammatic representation of an ultrasonic helium leak detector that is generally designated by the reference numeral 20 and that embodies the present invention. The leak detector 20 includes an acoustic cavity 22 having a pair of ultrasonic wave transmitters/receivers or transducers 24 and 26 at opposite side ends thereof. When a low speed air pump 28 is activated, pure air or an air/helium mixture is drawn through the cavity 22 depending on the state of a switch valve 30 that controls the flow of the air or air/helium mixture into the acoustic cavity 22. An electronic circuit 32 includes a pulser/receiver 34 that at selected time intervals causes one of the transmitters/receivers 24 and 26 (for example, the transmitter/receiver 24) to generate a high frequency ultrasonic wave across the acoustic cavity 22. This ultrasonic wave reflects back and forward across the acoustic cavity 22 between the pair of transmitters/receivers 24 and 26 such that the other of the transmitters/receivers 24 and 26 (for example, the transmitter/receiver 26) receives this wave and supplies a signal indicative of the reflected wave to the pulser/receiver 34 in the electronic circuit 32. The signal then is processed by the electronic circuit 32 such that the time of flight of the ultrasonic waves across the cavity 22 can be determined. Based on a comparison of this time of flight data of the ultrasonic waves when the gas mixture is flowing through the cavity 22 with the time of flight data of ultrasonic waves when air alone is flowing through the cavity 22, a determination is made as to the trace amount of certain gases (in the embodiment of FIG. 1, helium) within the gas/air mixture flowing through the cavity 22. The electronic circuit 32 then can display this determination and/or an audio signal can be provided if the amount of gases detected is above a certain threshold level.

The cavity 22 is an acoustic cavity having the transmitters/receivers 24 and 26 at opposite ends thereof. The leak detector 20 needs to be portable so the cavity 22 is relatively small in size with the distance between the transmitters/receivers 24 and 26 being, for example, approximately 0.64 cm. An inlet duct 36 provides an inlet air passageway into the cavity 22 from the switch valve 30 and an outlet duct 38 at the opposite end of the cavity 22 from the inlet duct 36 provides an outlet air passageway that is in communication with the air pump 28. Whenever a calibration button 40 is not activated, the switch valve 30 is placed in a pass through state to interconnect a sensor duct 42 to the inlet duct 36. As a result, any gas mixture flowing into an inlet 44 of the sensor duct 42, such as a mixture of air and helium, will be drawn into the duct 42 (as indicated by an arrow 42A) upon the actuation of the air pump 28. While a mixture of air and helium is disclosed as flowing in the duct 42, the leak detector 20 can be used to detect trace amounts of other gases in an air mixture. For example, these gases can include hydrogen, helium, organics, SF6, Radon or another gas where the speed of sound waves and the attenuation of those waves traveling through the gas mixture will be significantly different than the speed of sound waves and the attenuation of those waves traveling through air. The gas mixture flowing into the inlet 44 will be drawn through the duct 42, the switch valve 30, the acoustic cavity 22, the outlet duct 38 and the air pump 28 to a gas outlet duct 45 as indicated by an arrow 45A. As will be described hereinafter, determinations can be made as to the trace gases in that gas mixture as the gas mixture flows through the cavity 22.

In the event that a calibration is to be made as to ultrasonic waves traveling through ambient air, the calibration button 40 is activated. When the calibration button 40 is activated, the mode of the switch valve 30 is changed so that it no longer connects the sensor duct 42 to the inlet duct 36. Instead, the switch valve 30 connects an air inlet duct 46 to the inlet duct 36 such that ambient air flows through the air inlet duct 46 (as indicated by an arrow 46A), the switch valve 30 and the inlet duct 36 into the cavity 22 as long as the air pump 28 remains activated.

With ambient air flowing through the cavity 22, the leak detector 20 can be calibrated when the pulser/receiver 34 (the pulser/receiver 34 can be either a wide-band pulser/receiver or a single-frequency gated sine-wave function generator/receiver) activates one of the transmitters/receivers 24 and 26 (such as the transmitter/receiver 24) to generate an ultrasonic wave across the cavity 22 towards the opposite one of the transmitters/receivers 24 and 26 (such as the transmitter/receiver 26) as indicated by the double headed arrow 22A. The ultrasonic wave is a high-frequency wave so that better resolution of the wave is obtained and the pulse lasts for the least amount of time. For example, the wave can be either a pulse with a frequency of about 0.5 MHz and a duration of approximately 5 microseconds or a gated sine-wave with a frequency of 0.5 MHz and 6 to 10 cycles. The wave will reflect back and forward between the transmitters/receivers 24 and 26 in what might be termed a pitch-catch mode and thus through the air flowing through the cavity 22 from the inlet duct 36 to the outlet duct 38. As a result, the speed of the waves within the cavity 22 and the attenuation of those waves will be affected by the air flowing through the cavity 22.

The resultant waves will be received by the transmitter/receiver 26 and a signal indicative of those waves will be transmitted to the pulser/receiver 34 as indicated by arrows 24A and 26A. The received signal then is filtered by a gain-filter 48 to eliminate unwanted frequencies (such as noise) from those signals. For example, the gain-filter 48 can be in the form of a bandpass filter that will only allow signals in a frequency range between 0.450 and 0.550 MHz to be supplied to an analog averaging circuit 50. The analog averaging circuit 50 produces an average of the signals received over a number of pulsing cycles. This averaged signal then is supplied to a gated peak detector 52 so that the peak averaged signal within a selected time window set by the gate peak detector 52 can be determined. Based on this peak averaged signal and a timing period from a duration timer counter 54, a time of flight circuit 56 determines the time of flight of the ultrasonic waves being pulsed across the cavity 22. This time of flight data is then supplied to a calibration/differential circuit 58 in which the calibration information as to the time of flight data of the ultrasonic waves across the cavity 22 is stored.

Once the calibration sequence is completed, the calibration button 40 is released thereby changing the state of the switch valve 30. When so changed, air from the air inlet duct 46 will no longer be supplied to the inlet duct 36. Instead, a gas having a mixture of air and helium will be supplied to the inlet duct 36 from the sensor duct 42. As was the case when ambient air was flowing through the cavity 22, the pulser/receiver 34 will cause ultrasonic high frequency waves to be transmitted across the cavity 22 between the transmitters/receivers 24 and 26. The resultant waves echo between the transmitters/receivers 24 and 26 in a pitch-catch mode and a signal indicative of the waves will be supplied to the pulser/receiver 34 as indicated by the arrows 24A and 26A. As was the case when air was flowing through the cavity 22 and in the same manner that the time of flight was calculated for air flowing through the cavity 22, the time of flight of those waves can be calculated in the time of flight circuit 56 based on the signals and data being processed by the gain filter 48, the analog averaging circuit 50, the gated peak detector 52 and the timer counter 54. This time of flight data is supplied to the calibration/differential circuit 58 as is information as to the amplitude or the attenuation thereof of the waves. The difference between the time of flight of the ultrasonic wave in air and in the gas mixture can be calculated and the attenuation of those waves can be analyzed. Depending on the data received from the calibration/differential circuit 58, a detection threshold circuit 60 will cause an audible alarm 62 to be annunciated. The strength of the audible signal provided by the audible alarm 62 can be proportional to the differential of the time of flight being detected. In addition, the information as to the gas being detected in the gas/air mixture can be displayed on a mini-display 64.

With regard to the identification of the gas in the gas/air mixture, the time of flight differential between the propagation of the ultrasonic waves in the cavity 22 when ambient air is flowing through the cavity 22 and when a gas mixture of air and certain other gases is flowing through the cavity 22 can be used to determine what gas is present in the gas mixture. In this regard, the time of flight (TOF) that an ultrasonic wave takes to travel a particular distance is affected by the gas or gases through which the wave is traveling. In general, the sound velocity of waves in a gas is inversely proportional to the molecular weight of the gas. By way of illustration, the following table provides information as to the time of flight of the fifth reflection traveling through a cavity which is equivalent to a travel distance of approximately 11.43 cm, and how that time of flight differs when the sound waves are traveling through air alone or a gas mixed with air:

| Gases | Sound Speed m/sec | TOF μsec | TOF Difference μsec |
|---|---|---|---|
| He | 1015 | 112.6 | 217.7 |
| Ne | 454 | 251.8 | 78.5 |
| Ar | 322 | 355.0 | −24.7 |
| Kr | 223 | 512.6 | −182.3 |
| Xe | 177 | 654.8 | −323.7 |
| Air | 346 | 330.3 | 0.0 |
| $H_2$ | 1315 | 86.9 | 243.3 |
| $D_2$ | 930 | 122.9 | 207.4 |

Figure 2:
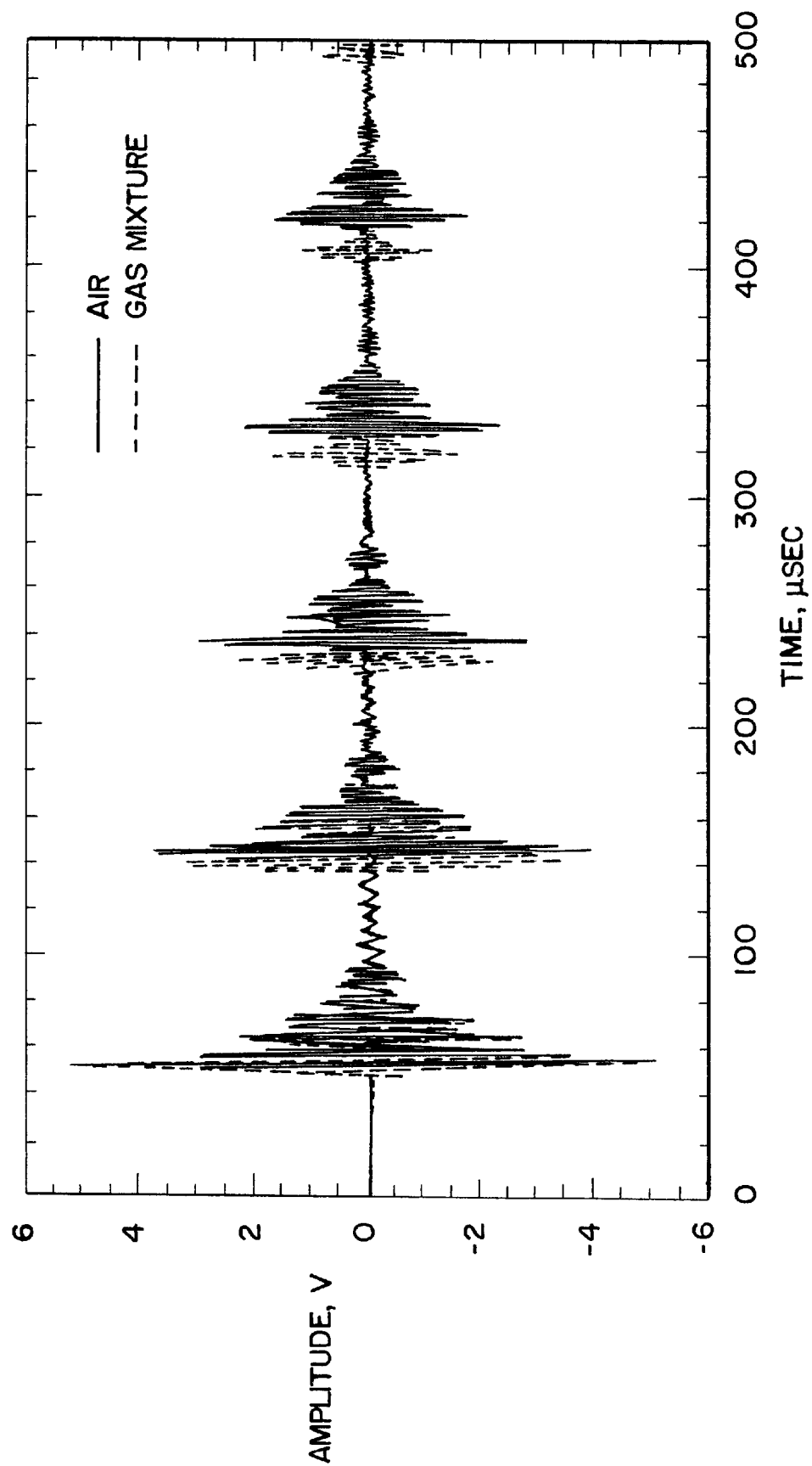
FIG. 2 is a graph showing the signals begin received from the transducers in an acoustic cavity like the cavity shown in FIGS. 1 and 3–4 as ultrasonic waves are reflected within the cavity.

As noted above, the width of the cavity 22 is relatively short in part because the leak detector 20 needs to be portable. Nevertheless, the leak detector 20 is highly sensitive to the time of flight of the ultrasonic waves traveling through the gas flowing through the cavity 22. This is in part due to the fact that each of the cycles of the signals being received by the pulser/receiver 34 is not analyzed. Instead, the waves are allowed to echo back and forward across the cavity 22 a number of times before the signals are analyzed. As a result, the effective width as opposed to the actual width of the cavity 22 is increased. More specifically, the electronic circuit 32 monitors a higher order reflection (e.g., the fifth reflection). In this regard, reference can be made to FIG. 2 of the drawings which shows signals being received from transducers like the transmitters/receivers 24 and 26 in acoustic cavities like the cavity 22 (in the case of FIG. 2, the signals are from two separate cavities, one for a gas mixture (dotted line) and the other air (solid line) (an example of a dual cavity monitor is the ultrasonic particulate monitor illustrated in FIG. 4)). As shown in the graph of FIG. 2, each consecutive reflection represents an additional path length over which the ultrasonic wave has traveled within the acoustic cavity and the higher order reflections (e.g., the fifth reflection) provide higher sensitivity even though the amplitude of the signal tends to decrease as the ultrasonic wave looses energy as it is being reflected back and forward across the cavity.

Figure 3:
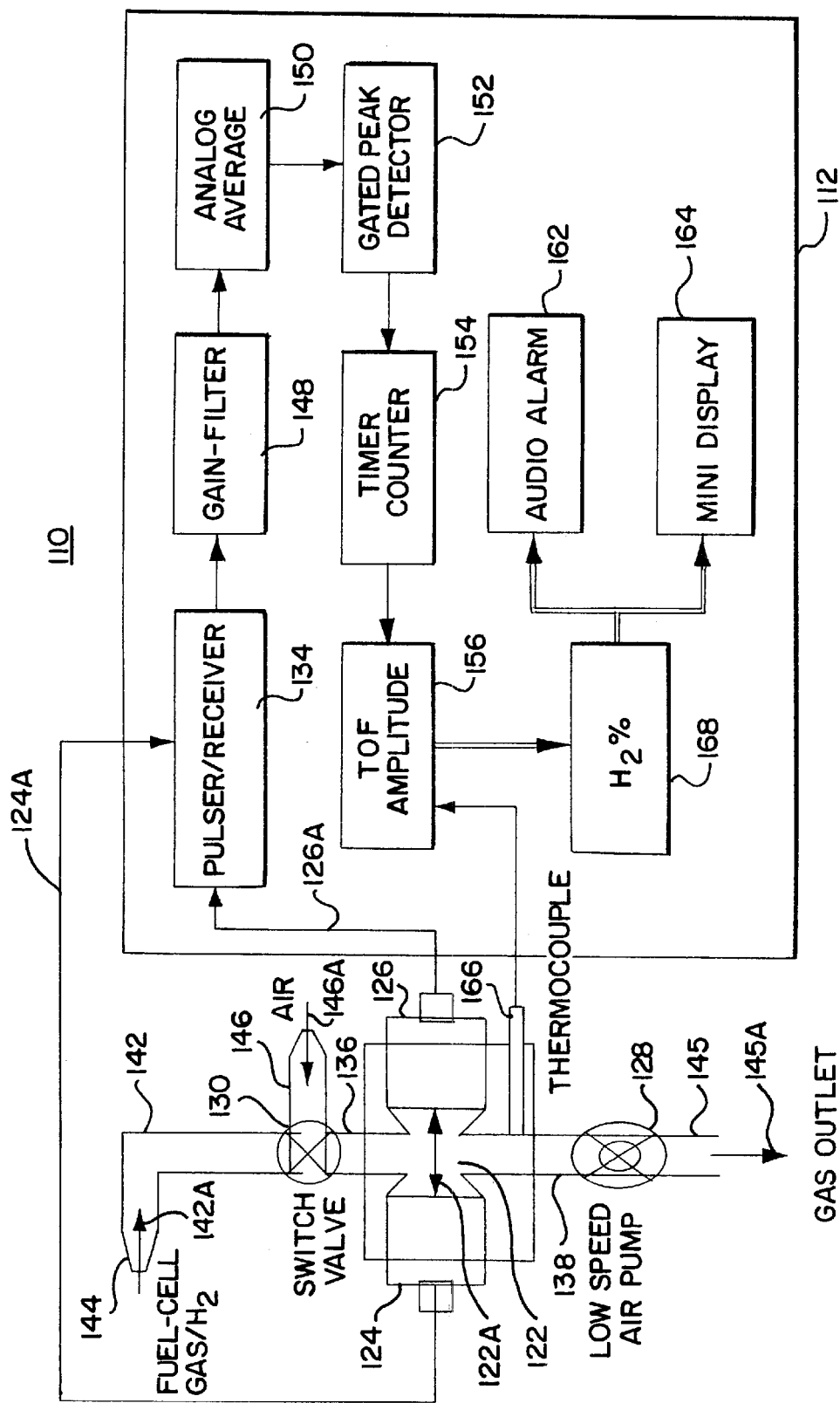
FIG. 3 is a diagrammatic view of an embodiment of the present invention which is an ultrasonic hydrogen monitor with the electronic circuit therefor shown in block diagram form.

An alternate embodiment of the present invention is disclosed in FIG. 3 of the drawings. In FIG. 3, therein is disclosed a diagrammatic representation of an ultrasonic hydrogen monitor that is generally designated by the reference numeral 110 and that also embodies the present invention. The ultrasonic hydrogen monitor 110 can be used to monitor the flow of hydrogen gas in connection with fuel cells. The ultrasonic hydrogen monitor 110 includes a number of the same components included in the helium leak detector 20 disclosed in FIG. 1 of the drawings. Consequently, the components of the ultrasonic hydrogen monitor 110 are referenced by the same reference numerals as the corresponding components in the helium leak detector 20 except that the quantity 100 has been added to the reference numerals.

The hydrogen monitor 110 includes an acoustic cavity 122 having a pair of ultrasonic wave transmitters/receivers or transducers 124 and 126 at opposite side ends thereof. When a low speed air pump 128 is activated, pure air or an air/hydrogen mixture is drawn through the cavity 122 depending on the state of a switch valve 130 that controls the flow of the air or air/hydrogen mixture into the acoustic cavity 122. An electronic circuit 112 includes a pulser/receiver 134 that at selected time intervals causes one of the transmitters/receivers 124 and 126 (for example, the transmitter/receiver 124) to generate a high frequency ultrasonic wave across the acoustic cavity 122. This ultrasonic wave reflects back and forward across the acoustic cavity 122 between the pair of transmitters/receivers 124 and 126 such that the other of the transmitters/receivers 124 and 126 (for example, the transmitter/receiver 126) receives this wave and supplies a signal indicative of the wave to the pulser/receiver 134 in the electronic circuit 112. The signal then is processed by the electronic circuit 112 such that the time of flight of the ultrasonic waves across the cavity 122 can be determined. Based on a comparison of this time of flight data of the ultrasonic waves when the gas mixture is flowing through the cavity 122 with the time of flight data of ultrasonic waves when air alone is flowing through the cavity 122, a determination is made as to the trace amount of certain gases (in the embodiment of FIG. 3, hydrogen) within the gas/air mixture flowing through the cavity 122. In this regard, the determination can take into account the temperature of the gas flowing through the cavity 122 because a thermocouple 166 supplies information to the electronic circuit 112 as to the temperature of the gas flowing through the cavity 122. The electronic circuit 112 then can display this determination and/or an audio signal can be provided if the amount of gases detected is above a certain threshold level.

The cavity 122 is an acoustic cavity, like the cavity 22 of FIG. 1, which has the transmitters/receivers 124 and 126 at opposite side ends thereof. The hydrogen monitor 110 needs to be portable so the cavity 122 is relatively small in size with the distance between the transmitters/receivers 124 and 126, for example, being approximately 0.64 cm. An inlet duct 136 provides an inlet air passageway into the cavity 122 from the switch valve 130 and an outlet duct 138 at the opposite end of the cavity 122 from the inlet duct 136 provides an outlet air passageway that is in communication with the air pump 128. Whenever it is necessary to calibrate the monitor 110, the switch valve 130 is placed in a pass through state to interconnect a sensor duct 142 to the inlet duct 136. As a result, any gas mixture flowing into an inlet 144 of the sensor duct 142, such as a mixture of air and hydrogen, will be drawn into the duct 142 (as indicated by an arrow 142A) upon the actuation of the air pump 128. While a mixture of air and hydrogen is disclosed as flowing in the duct 142, the hydrogen monitor 110 can be used to detect trace amounts of other gases in an air mixture. As noted above, these gases can include hydrogen, helium, organics, SF6, Radon or another gas where the speed of sound waves and the attenuation of those waves traveling through the gas mixture will be significantly different than the speed of sound waves and the attenuation of those waves traveling through air. The gas mixture flowing into the inlet 144 will be drawn through the duct 142, the switch valve 130, the acoustic cavity 122, the outlet duct 138 and the air pump 128 to a gas outlet duct 145 as indicated by an arrow 145A. As will be described hereinafter, determinations can be made as to the trace gases in that gas mixture as the gas mixture flows through the cavity 122.

In the event that a calibration is to be made as to ultrasonic waves traveling through ambient air, the mode of the switch valve 30 is changed so that it no longer connects the sensor duct 142 to the inlet duct 136. Instead, the switch valve 130 connects an air inlet duct 146 to the inlet duct 136 such that ambient air flows through the air inlet duct 146 (as indicated by an arrow 146A), the switch valve 130 and the inlet duct 136 into the cavity 122 as long as the air pump 128 remains activated.

With ambient air flowing through the cavity 122, the pulser/receiver 134 (the pulser/receiver 134 can be either a wide-band pulser/receiver or a single-frequency gated sine-wave function generator/receiver) activates one of the transmitters/receivers 124 and 126 (such as the transmitter/receiver 124) to generate an ultrasonic wave across the cavity 122 towards the opposite one of the transmitters/receivers 124 and 126 (such as the transmitter/receiver 126) as indicated by the double headed arrow 122A. The ultrasonic wave is a high-frequency wave so that better resolution of the wave is obtained and the pulse lasts for the least amount of time. For example, the wave can be either a pulse with a frequency of about 0.5 MHz and a duration of approximately 5 microseconds or a gated sine-wave with a frequency of 0.5 MHz and 6 to 10 cycles. The wave will reflect back and forward between the transmitters/receivers 124 and 126 in what might be termed a pitch-catch mode and thus through the air flowing through the cavity 122 from the inlet duct 136 to the outlet duct 138. As a result, the speed of the waves within the cavity 122 and the attenuation of those waves will be affected by the air flowing through the cavity 122.

The resultant waves will be received by the transmitter/receiver 126 and a signal indicative of those waves will be transmitted to the pulser/receiver 134 as indicated by arrows 124A and 126A. The received signal then is filtered by a gain-filter 148 to eliminate unwanted frequencies (such as noise) from those signals. For example, the gain-filter 148 can be in the form of a bandpass filter that will only allow signals in a frequency range between 0.450 and 0.550 MHz to be supplied to an analog averaging circuit 150. The analog averaging circuit 150 produces an average of the signals received over a number of pulsing cycles. This averaged signal then is supplied to a gated peak detector 152 so that the peak averaged signal within a selected time window set by the gate peak detector 152 can be determined. Based on this peak averaged signal and a timing period from a duration timer counter 154, a time of flight circuit 156 determines the time of flight of the ultrasonic waves being pulsed across the cavity 122 taking into the account the temperature of the air flowing in the outlet duct 138 as monitored by the thermocouple 166. This time of flight data is then supplied to a hydrogen determination circuit 168 in which the calibration information as to the time of flight information of the ultrasonic waves across the cavity 122 is stored.

Once the calibration sequence is completed, the state of the switch valve 130 is changed so that air from the air inlet duct 146 will no longer be supplied to the inlet duct 136. Instead, a gas having a mixture of air and hydrogen will be supplied to the inlet duct 136 from the sensor duct 142. As was the case when ambient air was flowing through the cavity 122, the pulser/receiver 134 will cause ultrasonic high frequency waves to be transmitted across the cavity 122 between the transmitters/receivers 124 and 126. The resultant waves echo between the transmitters/receivers 124 and 126 in a pitch-catch mode and a signal indicative of the waves will be supplied to the pulser/receiver 134 as indicated by the arrows 124A and 126A. As was the case when air was flowing through the cavity 122 and in the same manner that the time of flight was calculated for air flowing through the cavity 22, the time of flight of those waves can be calculated in the time of flight circuit 156 based on the signals and data being processed by the gain filter 148, the analog averaging circuit 150, the gated peak detector 152 and the timer counter 154. This time of flight data is supplied to the hydrogen determination circuit 168 as is information as to the amplitude of the waves. The difference between the time of flight of the ultrasonic wave in air and in the gas mixture containing hydrogen can be calculated and the attenuation of those waves can be analyzed. Depending on this data, the hydrogen determination circuit 168 will cause an audible alarm 162 to be annunciated. The strength of the audible signal provided by the audible alarm 162 can be proportional to the differential of the time of flight being detected. In addition, the information as to the gas being detected in the hydrogen/air mixture can be displayed on a mini-display 164 and the information from the thermocouple 166 can be used to provide information as the temperature of the hydrogen/air mixture flowing through the cavity 122.

As is discussed above with respect to the leak detector 20, the time of flight differential between the propagation of the ultrasonic waves in the cavity 122 when ambient air is flowing through the cavity 122 and when a gas mixture of air and certain other gases is flowing through the cavity 122 can be used to determine what gas is present in the gas mixture. As further discussed above, the width of the cavity 122 is relatively short in part because the hydrogen monitor 110 needs to be portable. Nevertheless, the hydrogen monitor 110 is highly sensitive to the time of flight of the ultrasonic waves traveling through the gas flowing through the cavity 122 in part due to the fact that each of the cycles of the signals being received by the pulser/receiver 134 is not analyzed. Instead, the waves are allowed to echo back and forward across the cavity 122 a number of times before the signals are analyzed. As a result, the effective width as opposed to the actual width of the cavity 122 is increased.

In this regard, a higher order reflection (e.g., the fifth reflection) is analyzed because as shown in FIG. 2 of the drawings, each consecutive reflection represents an additional path length over which the ultrasonic wave has traveled within the acoustic cavity and the higher order reflections (e.g., the fifth reflection) provide higher sensitivity even though the amplitude of the signal tends to decrease as the ultrasonic wave looses energy as it is being reflected back and forward across the cavity.

Figure 4:
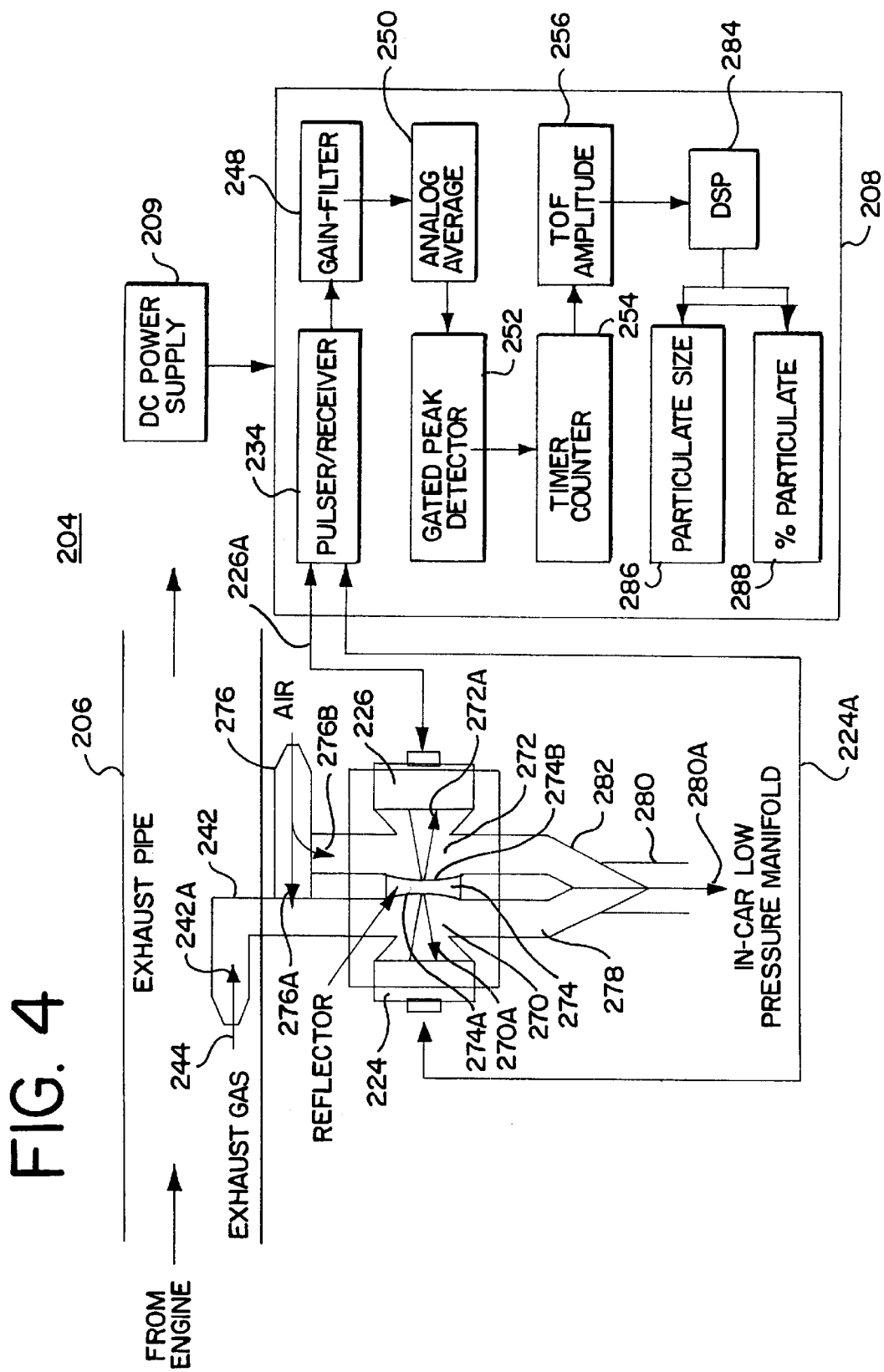
FIG. 4 is a diagrammatic view of an embodiment of the present invention which is an ultrasonic particulate monitor with the electronic circuit therefor shown in block diagram form.

Another alternate embodiment of the present invention is disclosed in FIG. 4 of the drawings. In FIG. 4, therein is disclosed a diagrammatic representation of an ultrasonic particulate monitor that is generally designated by the reference numeral 204 and that also embodies the present invention. The ultrasonic particulate monitor 204 can be used to monitor gases that are flowing in an exhaust pipe 206 of a diesel or CIDI engine. The ultrasonic particulate monitor 204 includes a number of the same components included in the ultrasonic hydrogen monitor 110 disclosed in FIG. 3 of the drawings. Consequently, the components of the ultrasonic particulate monitor 204 are referenced by the same reference numerals as the corresponding components in the ultrasonic hydrogen monitor 110 except that the quantity 100 has been added to the reference numerals.

The ultrasonic particulate monitor 204 includes a pair of acoustic cavities 270 and 272 separated by a double concave reflector lens 274. An ultrasonic wave transmitter/receiver or transducer 224 is located on an end of the cavity 270 opposite from a side 274A of the lens 274 and an ultrasonic wave transmitter/receiver or transducer 226 is located on an end of the cavity 272 opposite from a side 274B of the lens 274. Pure ambient air is drawn through the cavity 272 and a mixture of ambient air and exhaust gases flowing in the exhaust pipe 206 is drawn through the cavity 270. An electronic circuit 208 powered by a DC power supply 209 includes a pulser/receiver 234 that at selected time intervals causes the transmitters/receivers 224 and 226 to generate high frequency ultrasonic waves across the acoustic cavities 270 and 272. The ultrasonic wave from the transmitter/receiver 224 reflects back and forward across the acoustic cavity 270 between the transmitter/receiver 224 and the side 274A of the lens 274 and the ultrasonic wave from the transmitter/receiver 226 reflects back and forward across the acoustic cavity 272 between the transmitter/receiver 226 and the side 274B of the lens 274. In the case of the cavity 270, the transmitter/receiver 224 receives this wave and supplies a signal indicative of the wave to the pulser/receiver 234 in the electronic circuit 208 and in the case of the cavity 272, the transmitter/receiver 226 receives this wave and supplies a signal indicative of the wave to the pulser/receiver 234 in the electronic circuit 208. In this manner, the pulser/receiver 234 is continually receiving signals of the speed and amplitude of the sound waves through the exhaust gases/air mixture and the speed and amplitude of the sound waves through the air alone. The signals being received by the pulser/receiver 234 then is processed by the electronic circuit 208 such that the time of flight of and the amplitude of the ultrasonic waves across the cavities 270 and 272 can be determined. Based on a comparison of this time of flight data of and the amplitude of the ultrasonic waves propagating through the gas mixture flowing through the cavity 270 with the time of flight data of ultrasonic waves propagating through the ambient air flowing through the cavity 272, a determination is made as to the exhaust gases (in the embodiment of FIG. 4, particulates in the exhaust gases from a diesel or CIDI engine) within the gas/air mixture flowing through the cavity 270. The electronic circuit 208 then can display these determinations.

Unlike the leak detector 20 of FIG. 1 and the hydrogen monitor of FIG. 3, the ultrasonic particulate monitor 204 includes two acoustic cavities 270 and 272. However, these two cavities 270 and 272 function similarly to the cavities 22 and 122. More specifically, the cavity 270 is an acoustic cavity with the transmitter/receiver 224 at one opposite end of the cavity 270 and the side 274A of the lens 274 forming the other opposite end. Similarly, the cavity 272 is an acoustic cavity with the transmitter/receiver 226 at one opposite end of the cavity 270 and the side 274B of the lens 274 forming the other opposite end. The particulate monitor 204 needs to be portable so the cavities 270 and 272 are relatively small in size with the distance between the transmitter/receiver 224 and the lens side 274A and the distance between the transmitter/receiver 226 and the lens side 274B each, for example, being approximately 0.64 cm.

A sensor duct 242 provides an inlet air passageway into the cavity 270 from an inlet 244 and an air inlet duct 276 provides an inlet air passageway into the cavity 272 and also into the sensor duct 242. An outlet duct 278 at the opposite end of the cavity 270 from the sensor duct 242 provides an outlet air passageway for the cavity 270 that is in communication with a gas outlet duct 280. In a similar manner, an outlet duct 282 at the opposite end of the cavity 272 from the air inlet duct 276 provides an outlet air passageway for the cavity 272 that is in communication with the gas outlet duct 280. As is shown in FIG. 4, the gas outlet duct 280 may be connected to the low pressure vacuum manifold of the CIDI engine so that exhaust gas/air mixture is drawn through the cavity 270 and air is drawn through the cavity 272 whenever the engine is operating.

More specifically, exhaust gases flowing in the engine exhaust pipe 206 will be drawn through the inlet 244 and flow in the sensor duct 242 (as indicated by an arrow 242A) whenever the engine is operating. The gases flowing in the sensor duct 242 will combine with ambient air being drawn into the air inlet duct 276 (as indicated by an arrow 276A) and this exhaust gas and air mixture will flow through the cavity 270 between the transmitter/receiver 224 and the lens side 274A and through the outlet duct 278 to the gas outlet duct 280 (as indicated by an arrow 280A). In a similar manner, air flowing in the air inlet duct 276 will flow through the air inlet duct 276 (as indicated by an arrow 276B), the cavity 272 between the transmitter/receiver 226 and the lens side 274B and the outlet duct 282 to the gas outlet duct 280 (as indicated by an arrow 276A). In addition, the air flowing in the air inlet duct 276 will flow into the sensor duct 242 as indicated by the arrow 276A.

When the exhaust gas/air mixture flowing through the cavity 270 is to be analyzed, the pulser/receiver 234 (the pulser/receiver 234 can be either a wide-band pulser/receiver or a single-frequency gated sine-wave function generator/receiver) activates the transmitter/receiver 224 to generate an ultrasonic wave across the cavity 270 towards the lens side 274A on the opposite side of the cavity 270. The ultrasonic wave is reflected back and forward in what be termed as pulse-echo mode across the cavity 270 between the transmitter/receiver 224 and the lens side 274A as generally indicated by the arrow 270A. Likewise, the pulser/receiver 234 activates the transmitter/receiver 226 to generate an ultrasonic wave across the cavity 272 towards the lens side 274B on the opposite side of the cavity 272. The ultrasonic wave is reflected back and forward in a pulse-echo mode across the cavity 272 between the transmitter/receiver 226 and the lens side 274B as generally indicated by the arrow 272A. Each of these ultrasonic waves propagated across the cavities 270 and 272 is a high-frequency wave so that better resolution of the wave is obtained and the pulse lasts for the least amount of time. For example, the wave can be either a pulse with a frequency of about 0.5 MHz and a duration of approximately 5 microseconds or a gated sine-wave with a frequency of 0.5 MHz and 6 to 10 cycles.

In the case of the cavity 270, the wave will reflect back and forward between the transmitter/receiver 224 and the lens side 274A and thus through the exhaust gas/air mixture flowing through the cavity 270 from the sensor duct 242 to the outlet duct 278. As a result, the speed of the waves within the cavity 270 and the attenuation of those waves will be affected by the gas/air mixture flowing through the cavity 270. The resultant reflected waves will be received by the transmitter/receiver 224 and a signal indicative of those waves will be transmitted to the pulser/receiver 234 as indicated by an arrow 224A. In the case of the cavity 272, the wave will reflect back and forward between the transmitter/receiver 226 and the lens side 276A and thus through the ambient air flowing through the cavity 272 from the air inlet duct 276 to the outlet duct 282. As a result, the speed of the waves within the cavity 272 and the attenuation of those waves will be affected by the ambient air flowing through the cavity 272. The resultant reflected waves will be received by the transmitter/receiver 226 and a signal indicative of those waves will be transmitted to the pulser/receiver 234 as indicated by an arrow 226A. The received signals can be of the type shown in FIG. 2 where both the signal from the transmitter 224 (the dotted lines) and the transmitter 226 (the solid lines) are shown. These signals then are filtered by a gain-filter 248 to eliminate unwanted frequencies (such as noise) from those signals. For example, the gain-filter 248 can be in the form of a bandpass filter that will only allow signals in a frequency range between 0.450 and 0.550 MHz to be supplied to an analog averaging circuit 250. The analog averaging circuit 250 produces an average of the signals received over a number of pulsing cycles. This averaged signal then is supplied to a gated peak detector 252 so that the peak averaged signal within a selected time window set by the gate peak detector 252 can be determined. Based on this peak averaged signal and a timing period from a duration timer counter 254, a time of flight amplitude circuit 256 determines the time of flight of the ultrasonic waves being pulsed across the cavities 270 and 272. This time of flight data and data as to the amplitude of the waves then is supplied to a digital signal processor 284 in which a comparison is made with respect to the data being supplied based on the signals from the cavity 270 and the data being supplied based on signals from the cavity 272.

As is discussed above with respect to the leak detector 20 and the hydrogen monitor 110, the time of flight differential between the propagation of the ultrasonic waves in the cavity 272 through which ambient air is flowing and in the cavity 270 where a gas mixture of air and exhaust gases is flowing as well as information as to the amplitude of those waves can be used to determine what particulates are present in the exhaust gas/air mixture. As further discussed above, the width of the cavities 270 and 272 are relatively short in part because the particulate monitor 204 needs to be portable. Nevertheless, the particulate monitor 204 is highly sensitive to the time of flight and amplitude of the ultrasonic waves traveling through the gas flowing through the cavities 270 and 272 in part due to the fact that each of the cycles of the signals being received by the pulser/receiver 234 from respectively the transmitters/receivers 224 and 226 is not analyzed. Instead, the waves are allowed to echo back and forward across the cavity 270 and 272 a number of times before the signals are analyzed. As a result, the effective width as opposed to the actual width of the cavities 270 and 272 is increased. In this regard, a higher order reflection (e.g., the fifth reflection) is analyzed because as shown in FIG. 2 of the drawings, each consecutive reflection represents an additional path length over which the ultrasonic wave has traveled within the acoustic cavity and the higher order reflections (e.g., the fifth reflection) provide higher sensitivity even though the amplitude of the signal tends to decrease as the ultrasonic wave looses energy as it is being reflected back and forward in the cavity.

Based on the time of flight data from the time of flight circuit 256 and the amplitude of the signals received by the pulser/receiver 234, the size of the particulates in the exhaust gas flowing in the exhaust pipe 206 can be determined in the particulate size circuit 286 and the percentage of particulates in those exhaust gases can be determined by the particulate percentage circuit 288. This information can then be displayed.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. An ultrasonic gas analyzer for analyzing gases within a gas/air mixture, said ultrasonic gas analyzer comprising:
   an acoustic cavity having at least one transducer;
   an inlet for said acoustic cavity and an outlet for said acoustic cavity;
   an air mechanism relative to said outlet for drawing said gas/air mixture or air from said inlet through said acoustic cavity to said outlet; and
   electronic circuitry for controlling said transducer to propagate a high frequency ultrasonic wave across said acoustic cavity that is reflected within said acoustic cavity through said gas/air mixture or said air flowing through said acoustic cavity, said electronic circuitry receives from said transducer a signal indicative of said ultrasonic wave as it is reflected in said acoustic cavity and monitors a fifth reflection of said ultrasonic wave for determining said gas within said gas/air mixture based at least in part on the time of flight of said ultrasonic wave across said acoustic cavity when said gas/air mixture is flowing through said acoustic cavity and when said air is flowing through said cavity.

2. An ultrasonic gas analyzer as set forth in claim 1 wherein said ultrasonic wave is a pulsed wave having a frequency of about 0.5 MHz.

3. An ultrasonic gas analyzer as set forth in claim 1 wherein said ultrasonic wave is a single frequency gated sine-wave having a frequency of about 0.5 MHz.

4. An ultrasonic gas analyzer as set forth in claim 1 including a valve for controlling the flow of said gas/air mixture and said air through said inlet into said acoustic cavity.

5. An ultrasonic gas analyzer as set forth in claim 1 wherein said air mechanism is a low speed pump.

6. An ultrasonic gas analyzer as set forth in claim 1 including a pair of transmitters/receivers on opposite sides of said acoustic cavity, and wherein said electronic circuitry includes a signal generator and receiver to actuate at least one of said transmitters/receivers to generate said ultrasonic wave and to receive a signal indicative of said ultrasonic wave from at least the other of said transmitters/receivers as said ultrasonic wave is reflected between said transmitters/receivers in said acoustic cavity.

7. An ultrasonic gas analyzer as set forth in claim 1 wherein said electronic circuitry additionally monitors a higher order reflection of said ultrasonic wave to determine the gas within said gas/air mixture based at least in part on the time of flight of said ultrasonic wave across said acoustic cavity and the attenuation of said ultrasonic wave when said gas/air mixture is flowing through said acoustic cavity and when said air is flowing through said cavity.

8. An ultrasonic gas analyzer as set forth in claim 1 including a thermocouple mounted relative to the flow of the gas/air mixture or the air to provide said electronic circuit with data as to the temperature of the gas/air mixture or air flowing through said acoustic cavity.

9. An ultrasonic gas analyzer as set forth in claim 1 wherein said electronic circuit includes a signal generator and receiver to control said transducer to propagate said ultrasonic wave and to receive signals from said transducer indicative of said ultrasonic wave as it reflects within said acoustic cavity, a gain filter to eliminate unwanted frequencies within said signal, an analog averaging circuit to produce an averaged signal of said signal over a number of cycles, a gated peak detector for determining the peak of the averaged signal within a selected time window and a time of flight circuit for determining the time of flight of the peaked averaged signal.

10. An ultrasonic gas analyzer for analyzing gases within a gas/air mixture, said ultrasonic gas analyzer comprising:
    a pair of acoustic cavities separated by a reflector lens, each of said acoustic cavities including a transducer at one side end and a side of said reflector lens at the other side end of the acoustic cavity;
    an inlet for said acoustic cavities and an outlet for said acoustic cavities;
    an air mechanism relative to said outlet for drawing said gas/air mixture or air from said inlet through said acoustic cavity to said outlet; and
    electronic circuitry for controlling each of said transducers to propagate a high frequency ultrasonic wave across said acoustic cavities toward said reflector lens and to receive said ultrasonic wave as it is reflected from said lens through said gas/air mixture or said air flowing through said acoustic cavity, said electronic circuitry receives from each of said transducers a signal indicative of said ultrasonic wave as it is reflected in said acoustic cavity and monitors a higher order reflection of said ultrasonic wave to determine the gas within said gas/air mixture based at least in part on the time of flight of said ultrasonic wave across said acoustic cavity when said gas/air mixture is flowing through said acoustic cavity and when said air is flowing through said cavity.

11. An ultrasonic gas analyzer as set forth in claim 10 including a thermocouple mounted relative to the flow of the gas/air mixture or the air to provide said electronic circuit with data as to the temperature of the gas/air mixture or air flowing through said acoustic cavity.

12. An ultrasonic gas analyzer as set forth in claim 10 wherein said electronic circuit includes a signal generator and receiver to control said transducer to propagate said ultrasonic wave and to receive signals from said transducer indicative of said ultrasonic wave as it reflects within said acoustic cavity, a gain filter to eliminate unwanted frequencies within said signal, an analog averaging circuit to produce an averaged signal of said signal over a number of cycles, a gated peak detector for determining the peak of the averaged signal within a selected time window and a time of flight circuit for determining the time of flight of the peaked averaged signal.

13. An ultrasonic gas analyzer as set forth in claim 10 including a gas/air mixture inlet for one of said acoustic cavities and an air inlet for the other of said acoustic cavities such that said ultrasonic wave being propagated across one of said acoustic cavities travels through said gas/air mixture and said ultrasonic wave being propagated across the other of said acoustic cavities travels through said air mixture and said electronic circuit comparing the time of flight and amplitude of said ultrasonic wave traveling through said gas/air mixture to the time of flight and amplitude of said ultrasonic wave traveling through said air to determine the gas in said gas/air mixture.

14. An ultrasonic gas analyzer as set forth in claim 10 wherein said ultrasonic wave is a pulsed wave having a frequency of about 0.5 MHz.

15. An ultrasonic gas analyzer as set forth in claim 10 wherein said ultrasonic wave is a single frequency gated sine-wave having a frequency of about 0.5 MHz.

16. An ultrasonic gas analyzer as set forth in claim 10 including a valve for controlling the flow of said gas/air mixture and said air through said inlet into said acoustic cavity.

17. An ultrasonic gas analyzer as set forth in claim 10 wherein said air mechanism is a low speed pump.

18. A method of analyzing gases within a gas/air mixture comprising:
   providing a flow of said gas/air mixture through an acoustic cavity having at least one transducer;
   causing said transducer to propagate a high frequency ultrasonic wave across said acoustic cavity that is reflected within said acoustic cavity through said gas/air mixture;
   providing a gas/air signal from said transducer to an electronic circuitry which signal is indicative of said ultrasonic wave as it is reflected in said acoustic cavity through said gas/air mixture, said gas/air signal including signals indicative of a number of reflections of said ultrasonic wave;
   providing a flow of air through said acoustic cavity;
   causing said transducer to propagate a high frequency ultrasonic wave across said acoustic cavity that is reflected within said acoustic cavity through said air;
   providing an air signal from said transducer to an electronic circuitry that is indicative of said ultrasonic wave as it is reflected in said acoustic cavity through said air, said air signal including signals indicative of a number of reflections of said ultrasonic wave; and
   monitoring a fifth reflection of said ultrasonic wave of said gas and air signals to determine the gas within said gas/air mixture based at least on the time of flight of said ultrasonic wave across said acoustic cavity when said gas/air mixture is flowing through said acoustic cavity and when said air is flowing through said cavity.

19. A method of analyzing gases within a gas/air mixture as set forth in claim 18 wherein said ultrasonic wave is a pulsed wave having a frequency of about 0.5 MHz.

20. A method of analyzing gases within a gas/air mixture as set forth in claim 18 wherein said ultrasonic wave is a single frequency gated sine-wave having a frequency of about 0.5 MHz.

21. A method of analyzing gases within a gas/air mixture as set forth in claim 18 including a thermocouple mounted relative to the flow of the gas/air mixture or the air to provide with data as to the temperature of the gas/air mixture or air flowing through said acoustic cavity.

22. A method of analyzing gases within a gas/air mixture as set forth in claim 21 including a signal generator and receiver to control said transducer to propagate said ultrasonic wave and to receive signals from said transducer indicative of said ultrasonic wave as it reflects within said acoustic cavity, a gain filter to eliminate unwanted frequencies within said signal, an analog averaging circuit to produce an averaged signal of said signal over a number of cycles, a gated peak detector for determining the peak of the averaged signal within a selected time window and a time of flight circuit for determining the time of flight of the peaked averaged signal.

23. A method of analyzing gases within a gas/air mixture as set forth in claim 18 including additionally monitoring a higher order reflection of said ultrasonic wave to determine the gas within said gas/air mixture based at least in part on the time of flight of said ultrasonic wave across said acoustic cavity and the attenuation of said ultrasonic wave when said gas/air mixture is flowing through said acoustic cavity and when said air is flowing through said cavity.

24. A method of analyzing gases within a gas/air mixture comprising:
   providing a flow of said gas/air mixture through a pair of acoustic cavities separated by a reflector lens, each of said acoustic cavities including a transducer at one side end and a side of said reflector lens at the other side end of the acoustic cavity;
   causing each of said transducers to propagate a high frequency ultrasonic wave across said acoustic cavities toward said reflector lens and to receive said ultrasonic wave as it is reflected from said lens through said gas/air mixture;
   providing a gas/air signal from said transducer to an electronic circuitry which signal is indicative of said ultrasonic wave as it is reflected in said acoustic cavity through said gas/air mixture, said gas/air signal including signals indicative of a number of reflections of said ultrasonic wave;
   providing a flow of air through said acoustic cavity;
   causing said transducer to propagate a high frequency ultrasonic wave across said acoustic cavity that is reflected within said acoustic cavity through said air;
   providing an air signal from said transducer to an electronic circuitry that is indicative of said ultrasonic wave as it is reflected in said acoustic cavity through said air, said air signal including signals indicative of a number of reflections of said ultrasonic wave; and
   monitoring a higher order reflection of said gas and air signals to determine the gas within said gas/air mixture based at least on the time of flight of said ultrasonic wave across said acoustic cavity when said gas/air mixture is flowing through said acoustic cavity and when said air is flowing through said cavity.

* * * * *